United States Patent
Defossa et al.

(10) Patent No.: US 8,748,465 B2
(45) Date of Patent: Jun. 10, 2014

(54) PHENYLAMINO-BENZOXAZOLE SUBSTITUTED CARBOXYLIC ACIDS, METHOD FOR THEIR PRODUCTION AND USE THEREOF AS MEDICAMENTS

(71) Applicant: Sanofi, Paris (FR)

(72) Inventors: Elisabeth Defossa, Frankfurt am Main (DE); Markus Follmann, Frankfurt am Main (DE); Thomas Klabunde, Frankfurt am Main (DE); Viktoria Dietrich, Frankfurt am Main (DE); Gerhard Hessler, Frankfurt am Main (DE); Siegfried Stengelin, Frankfurt am Main (DE); Guido Haschke, Frankfurt am Main (DE); Andreas Herling, Frankfurt am Main (DE); Stefan Bartoschek, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/938,627

(22) Filed: Jul. 10, 2013

(65) Prior Publication Data

US 2013/0303578 A1    Nov. 14, 2013

Related U.S. Application Data

(63) Continuation of application No. 12/267,896, filed on Nov. 10, 2008, now abandoned, which is a continuation of application No. PCT/EP2007/003806, filed on Apr. 30, 2007.

(30) Foreign Application Priority Data

May 11, 2006  (DE) .......................... 10 2006 021 878

(51) Int. Cl.
*A61K 31/423*    (2006.01)
(52) U.S. Cl.
CPC .................................. *A61K 31/423* (2013.01)
USPC ......................................... 514/375; 514/377
(58) Field of Classification Search
CPC .................................................... A61K 31/423
USPC .................................................. 514/375, 377
See application file for complete search history.

(56) References Cited

U.S. PATENT DOCUMENTS

| | | | |
|---|---|---|---|
| 4,025,637 A | 5/1977 | Dunwell et al. | |
| 6,593,354 B2 | 7/2003 | Clark et al. | |

FOREIGN PATENT DOCUMENTS

| | | | |
|---|---|---|---|
| DE | 2450042 | | 4/1975 |
| WO | WO 91/19702 | | 12/1991 |
| WO | WO 94/08962 | | 4/1994 |
| WO | WO 98/40381 | | 9/1998 |
| WO | WO 00/49005 | | 8/2000 |
| WO | WO 2005/070906 | * | 8/2005 |
| WO | WO 2005/070920 | | 8/2005 |

OTHER PUBLICATIONS

Azam et al., 'Antioxidant and prooxidant properties of caffeine, theobromine and xanthine,' Med. Sci. Monit. 9(9): BR325-330 (2003).
Gavezzotti, 'Are Crystal Structures Predictable?,' Acc. Chem. Res. 27:309-314 (1994).
Vippagunta et al., 'Crystalline solids,' Adv. Drug Del. Rev. 48:3-26 (2001).
Itoh et al., Free fatty acids regulate insulin secretion from pancreatic beta cells through GPR40, Nature 422:173-176 (2003).
Feng et al., 'GPR40: a therapeutic target for mediating insulin secretion (review),' Int. J. Mol. Med. 30(6):1261-6 (2012) (abstract only).
Araki et al., 'GPR40-induced insulin secretion by the novel agonist TAK-875: first clinical findings in patients with type 2 diabetes,' Diabetes Obes. Metab. 14(3):271-8(2012).
Office Action as mailed on Apr. 22, 2010, in U.S. Appl. No. 12/267,896.
Office Action as mailed on Jun. 3, 2010, in U.S. Appl. No. 12/267,896.
Office Action as mailed on Sep. 13, 2010, in U.S. Appl. No. 12/267,896.
Office Action as mailed on Apr. 10, 2013, in U.S. Appl. No. 12/267,896.

* cited by examiner

*Primary Examiner* — Noble Jarrell
*Assistant Examiner* — Valerie Rodriguez-Garcia

(57) ABSTRACT

This invention relates to a compound of formula I,

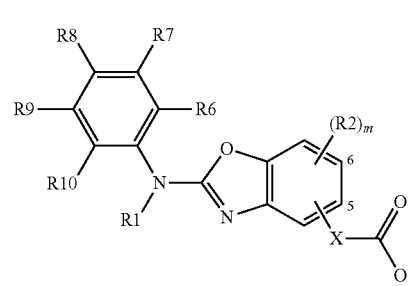

wherein R1, R2, R6, R7, R8, R9, R10, m and X are as defined herein, or a physiologically tolerated salt thereof, its pharmaceutical composition and use for lowering blood glucose, treating diabetes, or increasing insulin release.

12 Claims, No Drawings

PHENYLAMINO-BENZOXAZOLE SUBSTITUTED CARBOXYLIC ACIDS, METHOD FOR THEIR PRODUCTION AND USE THEREOF AS MEDICAMENTS

This application is a continuation of U.S. patent application Ser. No. 12/267,896, filed Nov. 10, 2008, which is a Continuation of International Application No. PCT/EP2007/003806, filed Apr. 30, 2007, both of which are incorporated herein by reference in their entirety.

FIELD OF THE INVENTION

The invention relates to phenylaminobenzoxazole-substituted carboxylic acids and their physiologically tolerated salts.

BACKGROUND OF THE INVENTION

Compounds of similar structure have been described in the prior art (see WO 94/08962).

The invention was based on the object of providing compounds which display a therapeutically utilizable effect. The object was in particular to find novel compounds suitable for the treatment of hyperglycemia and diabetes.

SUMMARY OF THE INVENTION

The invention therefore relates to compounds of the formula I,

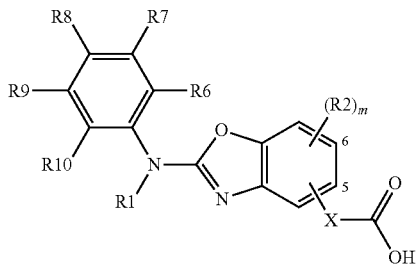

I in which the meanings are

R1 H or $(C_1-C_6)$-alkyl;
R6, R7, R8, R9, R10, independently of one another H, F, Cl, Br, CN, CF$_3$, OH, OCF$_3$, OCHF$_2$, SCH$_3$, SCF$_3$, phenyl, Ophenyl, COOH, COO—$(C_1-C_6)$-alkyl, CO—$(C_1-C_6)$-alkyl, $(C_1-C_6)$-alkyl, O—$(C_1-C_6)$-alkyl, OBn, SO$_3$H, SO$_2$NR3R4, NR3R4 or SO$_2$—N-piperidinyl, where alkyl and phenyl may be substituted one or more times by R2, and where in each case two of the radicals R6, R7, R8, R9, R10, in adjacent position on the phenyl ring may together form a radical —O—CH$_2$—O—, —O—(CH$_2$)$_2$—O— or —CH═CH—CH═CH—;
m 0, 1, 2 or 3;
X bond, $(C_2-C_{10})$-alkylene, $(C_3-C_{12})$-cycloalkyl, $(C_1-C_8)$-alkylene-$(C_3-C_{12})$-cycloalkyl-$(C_1-C_8)$-alkylene, $(C_1-C_8)$-alkylene-$(C_3-C_{12})$-cycloalkyl, $(C_3-C_{12})$-cycloalkyl-$(C_1-C_8)$-alkylene, $(C_2-C_8)$-alkenylene-$(C_3-C_{12})$-cycloalkyl-$(C_1-C_8)$-alkylene, $(C_1-C_8)$-alkylene-$(C_3-C_{12})$-cycloalkyl-$(C_2-C_8)$-alkenylene, $(C_2-C_8)$-alkenylene-$(C_3-C_{12})$-cycloalkyl, $(C_3-C_{12})$-cycloalkyl-$(C_2-C_8)$-alkenylene, $(C_2-C_{10})$-alkenylene or $(C_2-C_{10})$-alkynylene, where alkylene, cycloalkyl, alkenylene and alkynylene may be substituted one or more times by R5;
R2 OH, F, Cl, Br, CN, OCH$_3$, OCF$_3$, CH$_3$, CF$_3$, $(C_1-C_6)$-alkyl or O—$(C_1-C_6)$-alkyl, where alkyl may be substituted one or more times by OH, F, Cl, Br or CN;
R3, R4 independently of one another H or $(C_1-C_6)$-alkyl, where alkyl may be substituted one or more times by OH, F, Cl or Br;
R5 NH$_2$, NH$(C_1-C_4)$-alkyl, N[$(C_1-C_4)$-alkyl]$_2$, F, Cl, Br, CN, OH, O—$(C_1-C_6)$-alkyl, $(C_1-C_6)$-alkyl, $(C_2-C_6)$-alkenyl or $(C_2-C_6)$-alkynyl;
and the physiologically tolerated salts thereof.

DETAILED DESCRIPTION OF THE INVENTION

Preference is given to compounds of the formula I in which one or more radicals have the following meanings:
R1 H or $(C_1-C_6)$-alkyl;
R6, R7, R8, R9, R10, independently of one another H, F, Cl, Br, CF$_3$, OCH$_3$, OCF$_3$, OCHF$_2$, SCH$_3$, SCF$_3$, phenyl, $(C_1-C_6)$-alkyl, O—$(C_1-C_6)$-alkyl or NR3R4, where alkyl and phenyl may be substituted one or more times by R2, and where in each case two of the radicals R6, R7, R8, R9, R10 in adjacent position on the phenyl ring may together form a radical —CH═CH—CH═CH—;
m 0;
X $(C_2-C_{10})$-alkylene, where alkylene may be substituted one or more times by R5;
R3, R4 independently of one another H or $(C_1-C_6)$-alkyl;
R5 NH$_2$, NH$(C_1-C_4)$-alkyl, N[$(C_1-C_4)$-alkyl]$_2$, F, Cl, Br, CN, OH, O—$(C_1-C_6)$-alkyl, $(C_1-C_6)$-alkyl, $(C_2-C_6)$-alkenyl or $(C_2-C_6)$-alkynyl;
and the physiologically tolerated salts thereof.

Particular preference is given to compounds of the formula I in which one or more radicals have the following meanings:
R1 H;
R6, R7, R8, R9, R10, independently of one another H, F, Cl, Br, CF$_3$, OCH$_3$, OCF$_3$, OCHF$_2$, SCH$_3$, SCF$_3$, phenyl, $(C_1-C_6)$-alkyl, O—$(C_1-C_6)$-alkyl or NR3R4, where alkyl and phenyl may be substituted one or more times by R2, and where in each case two of the radicals R6, R7, R8, R9, R10 in adjacent position on the phenyl ring may together form a radical —CH═CH—CH═CH—;
m 0, 1, 2 or 3;
X —(CH$_2$)$_2$—;
R2 F, Cl, Br, CN, OCH$_3$, OCF$_3$, CH$_3$, CF$_3$, $(C_1-C_6)$-alkyl or O—$(C_1-C_6)$-alkyl, where alkyl may be substituted one or more times by OH, F, Cl, Br or CN;
R3, R4 independently of one another H or $(C_1-C_6)$-alkyl;
and the physiologically tolerated salts thereof.

If radicals or substituents may occur more than once in the compounds of the formulae I, they may all independently of one another have the stated meaning and be identical or different.

The alkyl, alkenyl, alkynyl, alkylene, alkenylene and alkynylene radicals in the radicals X, R1, R2, R3, R4, R5, R6, R7, R8, R9 and R10 may be either straight-chain or branched.

The invention relates to compounds of the formula I in the form of their salts, racemates, racemic mixtures and pure enantiomers, and diastereomers and mixtures thereof.

Physiologically tolerated salts are, because their solubility in water is greater than that of the initial or basic compounds, particularly suitable for medical applications. These salts must have a physiologically tolerated anion or cation. Suitable physiologically tolerated acid addition salts of the compounds of the invention are salts of inorganic acids such as hydrochloric acid, hydrobromic, phosphoric, metaphosphoric, nitric, sulfonic and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acids. The chlorine salt is particularly preferably used for medical purposes.

Suitable physiologically tolerated basic salts are ammonium salts, alkali metal salts (such as sodium and potassium salts), alkaline earth metal salts (such as magnesium and calcium salts), zinc salts, and salts of trometamol (2-amino-2-hydroxymethyl-1,3-propanediol), diethanolamine, lysine, arginine, choline, meglumine or ethylenediamine salts.

Salts with a physiologically untolerated anion or cation likewise belong within the framework of the invention as useful intermediates for preparing or purifying physiologically tolerated salts and/or for use in nontherapeutic, for example in vitro applications.

A further aspect of this invention are prodrugs of the compounds of the invention. Such prodrugs can be metabolized in vivo to a compound of the invention. These prodrugs may themselves be active or not.

The compounds of the invention may also exist in various polymorphous forms, e.g. as amorphous and crystalline polymorphous forms. All polymorphous forms of the compounds according to the invention belong within the framework of the invention and are a further aspect of the invention.

All references to "compound(s) of formula (I)" hereinafter refer to compound(s) of the formula (I) as described herein, and the salts and solvates thereof as described herein.

The compounds of the formula (I) and the physiologically tolerated salts thereof represent ideal pharmaceuticals for the treatment of elevated lipid concentrations in the blood, the metabolic syndrome, diabetes, insulin resistance, dysregulation of LDL, HLD and VLDL or cardiovascular disorders and lipid metabolism disorders, especially hyperlipidemia. The compound(s) of the formula (I) can also be administered in combination with further active ingredients.

The amount of a compound of formula (I) necessary to achieve the desired biological effect depends on a number of factors, for example the specific compound chosen, the intended use, the mode of administration and the clinical condition of the patient. The daily dose is generally in the range from 0.1 mg to 100 mg (typically from 0.1 mg to 50 mg) per day and per kilogram of body weight, for example 0.1-10 mg/kg/day. Tablets or capsules may contain, for example, from 0.01 to 100 mg, typically from 0.02 to 50 mg. For the prophylaxis or therapy of the abovementioned conditions, the compounds of formula (I) may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula (I). The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral and peroral (for example sublingual) administration, although the most suitable mode of administration depends in each individual case on the nature and severity of the condition to be treated and on the nature of the compound of formula (I) used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contains a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Combinations with other Medicaments

The compounds of the invention can be administered alone or in combination with one or more further pharmacologically active substances which have, for example, beneficial effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Further examples of active ingredients suitable for combination products are in particular: All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. They may be combined with the compound of the invention of the formula I in particular for a synergistic improvement in the effect. The active ingredient combination can be administered either by separate administration of the active ingredients to the patient or in the form of combination products in which a plurality of active ingredients is present in a pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964 or those described in WO2005005477 (Novo Nordisk), fast-acting insulins (see U.S. Pat. No. 6,221,633), inhalable insulins such as, for example, Exubera® or oral insulins such as, for example, IN-105 (Nobex) or Oral-lyn™ (Generex Biotechnology), GLP-1 derivatives such as, for example, exenatide, liraglutide or those which have been disclosed in WO98/08871 or WO2005027978 of Novo Nordisk A/S, in WO01/04156 of Zealand or in WO00/34331 of Beaufour-Ipsen, pramlintide acetate (Symlin; Amylin Pharmaceuticals), and orally effective hypoglycemic active ingredients.

The orally effective hypoglycemic active ingredients include preferably sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of glucose transporter 4 (GLUT4),
inhibitors of glutamine-fructose-6-phosphate amidotransferase (GFAT),
GLP-1 agonists,
potassium channel openers such as, for example, those which have been disclosed in WO 97/26265 and WO 99/03861 of Novo Nordisk A/S,
inhibitors of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption,
inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and active ingredients which act on the ATP-dependent potassium channel of the beta cells.

In one embodiment of the invention, the compound of the formula I is administered in combination with an HMGCoA reductase inhibitor such as simvastatin, fluvastatin, pravastatin, lovastatin, atorvastatin, cerivastatin, rosuvastatin or L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692), MD-0727 (Microbia Inc., WO2005021497) or with compounds as described in WO2002066464 (Kotobuki Pharmaceutical Co. Ltd.), WO2005062824 (Merck & Co.) or WO2005061451 and WO2005061452 (AstraZeneca AB).

In one embodiment of the invention, the compound of the formula I is administered in combination with a PPAR gamma agonist such as, for example, rosiglitazone, pioglitazone, JTT-501, GI 262570, R-483 or CS-011 (rivoglitazone).

In one embodiment of the invention, the compound of the formula I is administered in combination with a PPAR alpha agonist such as, for example, GW9578, GW-590735, K-111, LY-674, KRP-101 or DRF-10945.

In one embodiment of the invention, the compound of the formula I is administered in combination with a mixed PPAR alpha/gamma agonist such as, for example, muraglitazar, tesaglitazar, naveglitazar, LY-510929, ONO-5129, E-3030, AVE 8042, AVE 8134, AVE 0847, or as described in PCT/US 00/11833, PCT/US 00/11490, DE10142734.4 or in J. P. Berger et al., TRENDS in Pharmacological Sciences 28(5), 244-251, 2005.

In one embodiment of the invention, the compound of the formula I is administered in combination with a PPAR delta agonist such as, for example, GW-501516.

In one embodiment of the invention, the compound of the formula I is administered in combination with metaglidasen or with MBX-2044 or other partial PPAR gamma agonists/antagonists.

In one embodiment of the invention, the compound of the formula I is administered in combination with a fibrate such as, for example, fenofibrate, clofibrate or bezafibrate.

In one embodiment of the invention, the compound of the formula I is administered in combination with an MTP inhibitor such as, for example, implitapide, BMS-201038, R-103757 or those described in WO2005085226.

In one embodiment of the invention, the compound of the formula I is administered in combination with a CETP inhibitor such as, for example, torcetrapib or JTT-705.

In one embodiment of the invention, the compound of the formula I is administered in combination with a bile acid absorption inhibitor (see, for example, U.S. Pat. Nos. 6,245, 744, 6,221,897 or WO00/61568), such as, for example, HMR 1741 or those as described in DE 10 2005 033099.1 and DE 10 2005 033100.9.

In one embodiment of the invention, the compound of the formula I is administered in combination with a polymeric bile acid adsorbent such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those as described in WO2005097738.

In one embodiment of the invention, the compound of the formula I is administered in combination with Omacor® (omega-3 fatty acids; highly concentrated ethyl esters of eicosapentaenoic acid and of docosahexaenoic acid).

In one embodiment of the invention, the compound of the formula I is administered in combination with an ACAT inhibitor such as, for example, avasimibe.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor such as, for example, SB-204990.

In one embodiment of the invention, the compound of the formula I is administered in combination with a squalene synthetase inhibitor such as, for example, BMS-188494 or as described in WO2005077907.

In one embodiment of the invention, the compound of the formula I is administered in combination with a lipoprotein (a) antagonist such as, for example, gemcabene (CI-1027).

In one embodiment of the invention, the compound of the formula I is administered in combination with an HM74A receptor agonist such as, for example, nicotinic acid.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment of the invention, the compound of the formula I is administered in combination with a sulfonylurea such as, for example, tolbutamide, glibenclamide, glipizide or glimepiride.

In one embodiment of the invention, the compound of the formula I is administered in combination with a biguanide such as, for example, metformin.

In another embodiment of the invention, the compound of the formula I is administered in combination with a meglitinide such as, for example, repaglinide or nateglinide.

In one embodiment of the invention, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment of the invention, the compound of the formula I is administered in combination with an α-glucosidase inhibitor such as, for example, miglitol or acarbose.

In one embodiment of the invention, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment of the invention, the compound of the formula I is administered in combination with an inhibitor of glycogen phosphorylase, such as, for example, PSN-357 or FR-258900 or those as described in WO2003084922, WO2004007455, WO2005073229-31 or WO2005067932.

In one embodiment of the invention, the compound of the formula I is administered in combination with glucagon receptor antagonists such as, for example, A-770077, NNC-25-2504 or as described in WO2004100875 or WO2005065680.

In one embodiment of the invention, the compound of the formula I is administered in combination with activators of glucokinase, such as, for example, RO-4389620, LY-2121260 (WO2004063179), PSN-105, PSN-110, GKA-50 or those as described for example by Prosidion in WO2004072031, WO2004072066, WO 05103021 or WO 06016178, by Roche in WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, US 04067939 or WO 04052869, by Novo Nordisk in EP 1532980, WO 03055482, WO 04002481, WO 05049019, WO 05066145 or WO 05123132, by Merck/Banyu in WO 03080585, WO03097824, WO 04081001, WO 05063738 or WO 05090332, by Eli Lilly in WO 04063194, or by Astra Zeneca in WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment of the invention, the compound of the formula I is administered in combination with an inhibitor of gluconeogenesis, such as, for example, FR-225654.

In one embodiment of the invention, the compound of the formula I is administered in combination with inhibitors of fructose-1,6-bisphosphatase (FBPase), such as, for example, CS-917.

In one embodiment of the invention, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment of the invention, the compound of the formula I is administered in combination with inhibitors of glutamine-fructose-6-phosphate amidotransferase (GFAT), as are described for example in WO2004101528.

In one embodiment of the invention, the compound of the formula I is administered in combination with inhibitors of dipeptidylpeptidase IV (DPP-IV), such as, for example, vildagliptin (LAF-237), sitagliptin (MK-0431), saxagliptin (BMS-477118), GSK-823093, PSN-9301, SYR-322, SYR-619, TA-6666, TS-021, GRC-8200, GW-825964× or as are described in WO2003074500, WO2003106456, WO200450658, WO2005058901, WO2005012312, WO2005012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of the formula I is administered in combination with inhibitors of 11-beta-hydroxysteroid dehydrogenase 1 (11β-HSD1), such as, for example, BVT-2733 or those as are described for example in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004065351, WO2004089367, WO2004089380, WO2004089470-71, WO2004089896, WO2005016877 or WO2005097759.

In one embodiment of the invention, the compound of the formula I is administered in combination with inhibitors of protein tyrosine phosphatase 1B (PTP1B), as are described for example in WO200119830-31, WO200117516, WO2004506446, WO2005012295, PCT/EP2005/005311, PCT/EP2005/005321, PCT/EP2005/007151, PCT/EP2005/ or DE 10 2004 060542.4.

In one embodiment of the invention, the compound of the formula I is administered in combination with modulators of the sodium-dependent glucose transporter 1 or 2 (SGLT1, SGLT2), such as, for example, KGA-2727, T-1095, SGL- 0010, AVE 2268 and SAR 7226 or as are described for example in WO2004007517, WO200452903, WO200452902, PCT/EP2005/005959, WO2005085237, JP2004359630 or by A. L. Handlon in Expert Opin. Ther. Patents (2005) 15(11), 1531-1540.

In one embodiment of the invention, the compound of the formula I is administered in combination with inhibitors of hormone-sensitive lipase (HSL) as described for example in WO2005073199.

In one embodiment of the invention, the compound of the formula I is administered in combination with inhibitors of acetyl-CoA carboxylase (ACC), such as, for example, those as described in WO199946262, WO200372197, WO2003072197 or WO2005044814.

In one embodiment of the invention, the compound of the formula I is administered in combination with an inhibitor of phosphoenolpyruvate carboxykinase (PEPCK), such as, for example, those as described in WO2004074288.

In one embodiment of the invention, the compound of the formula I is administered in combination with an inhibitor of glycogen synthase kinase 3 beta (GSK-3 beta), as described for example in US2005222220, WO2005085230, PCT/EP2005/005346, WO2003078403, WO2004022544, WO2003106410, WO2005058908, US20050038023, WO2005009997, US2005026984, WO2005000836, WO2004106343, EP1460075, WO2004014910, WO2003076442, WO2005087727 or WO2004046117.

In one embodiment of the invention, the compound of the formula I is administered in combination with an inhibitor of protein kinase C beta (PKC beta), such as, for example, ruboxistaurin.

In one embodiment of the invention, the compound of the formula I is administered in combination with an endothelin A receptor antagonist such as, for example, avosentan (SPP-301).

In one embodiment of the invention, the compound of the formula I is administered in combination with inhibitors of "I-kappaB kinase" (IKK inhibitors), as are described for example in WO2001000610, WO2001030774, WO2004022553 or WO2005097129.

In one embodiment of the invention, the compound of the formula I is administered in combination with modulators of the glucocorticoid receptor, like those described for example in WO2005090336.

In a further embodiment of the invention, the compound of the formula I is administered in combination with CART modulators (see "Cocaine-amphetamine-regulated transcript influences energy metabolism, anxiety and gastric emptying in mice" Asakawa, A. et al.:

Hormone and Metabolic Research (2001), 33(9), 554-558);
NPY antagonists such as, for example, naphthalene-1-sulfonic acid {4-[(4-aminoquinazolin-2-ylamino)methyl]cyclohexylmethyl}amide hydrochloride (CGP 71683A);
peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424;
cannabinoid receptor 1 antagonists such as, for example, rimonabant, SR147778 or those as are described for example in EP 0656354, WO 00/15609, WO02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509 or WO2005077897;

MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076 or WO2004072077;

orexin receptor antagonists (e.g. 1-(2-methylbenzoxazol-6-yl)-3-[1,5]naphthyridin-4-ylurea hydrochloride (SB-334867-A) or those as are described for example in WO200196302, WO200185693, WO2004085403 or WO2005075458);

histamine H3 receptor agonists (e.g. 3-cyclohexyl-1-(4,4-dimethyl-1,4,6,7-tetrahydroimidazo[4,5-c]pyridin-5-yl)propan-1-one oxalic acid salt (WO 00/63208) or those as are described in WO200064884, WO2005082893);

CRF antagonists (e.g. [2-methyl-9-(2,4,6-trimethylphenyl)-9H-1,3,9-triazafluoren-4-yl]dipropylamine (WO 00/66585));

CRF BP antagonists (e.g. urocortin);

urocortin agonists;

β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002002744, WO2003004027 or FR2868780);

CCK-A agonists (such as, for example, {2-[4-(4-chloro-2,5-dimethoxyphenyl)-5-(2-cyclo-hexylethyl)thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (e.g. dexfenfluramine);

mixed serotoninergic and noradrenergic compounds (e.g. WO 00/71549);

5-HT receptor agonists, e.g. 1-(3-ethylbenzofuran-7-yl)piperazine oxalic acid salt (WO 01/09111);

5-HT2C receptor agonists (such as, for example, APD-356, BVT-933 or those as are described in WO200077010, WO20077001-02, WO2005019180, WO2003064423, WO200242304 or WO2005082859);

5-HT6 receptor antagonists as are described for example in WO2005058858;

bombesin receptor agonists (BRS-3 agonists);

galanin receptor antagonists;

growth hormone (e.g. human growth hormone or AOD-9604);

growth hormone-releasing compounds (tertiary butyl 6-benzyloxy-1-(2-diisopropyl-aminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO2005030734;

TRH agonists (see, for example, EP 0 462 884);

uncoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (like those described for example in WO 00/40569);

inhibitors of diacylglycerol O-acyltransferases (DGATs) as described for example in US2004/0224997, WO2004094618, WO200058491, WO2005044250, WO2005072740, JP2005206492 or WO2005013907;

inhibitors of fatty acid synthase (FAS) such as, for example, C75 or those as described in WO2004005277;

oxyntomodulin;

oleoyl-estrone or thyroid hormone receptor agonists such as, for example: KB-2115 or those as described in WO20058279, WO200172692, WO200194293, WO2003084915, WO2004018421 or WO2005092316.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine.

In one embodiment of the invention, the further active ingredient is mazindole or phentermine.

In one embodiment of the invention, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

It will be understood that every suitable combination of the compounds of the invention with one or more of the aforementioned compounds and optionally one or more further pharmacologically active substances will be regarded as falling within the protection conferred by the present invention.

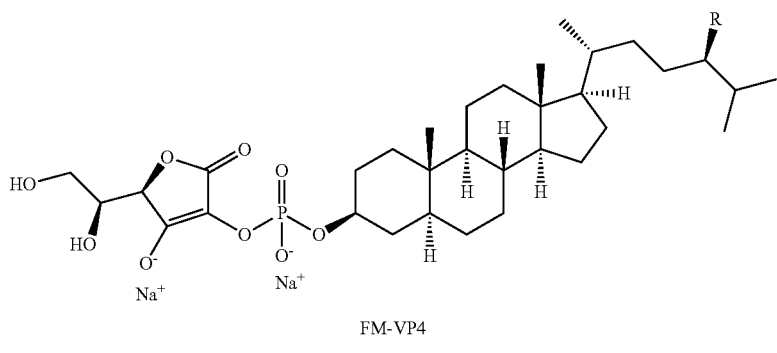

FM-VP4

R = CH$_3$; CH$_2$—CH$_3$

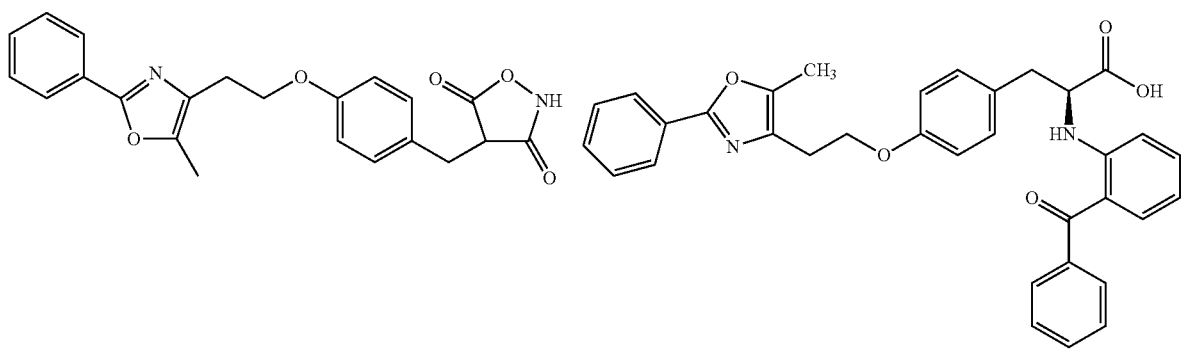

JTT-501

GI 262570

-continued
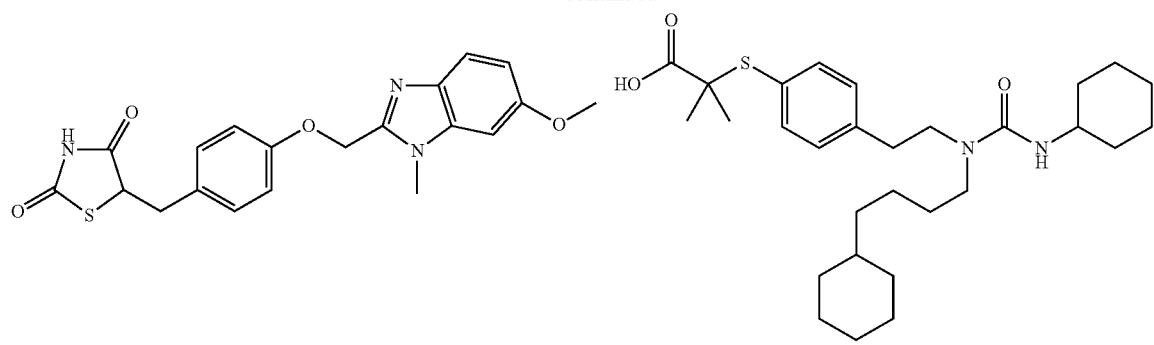
CS-011
Rivoglitazone
GW-9578
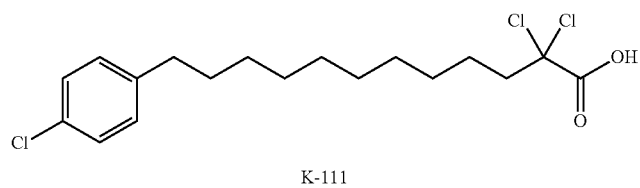
K-111
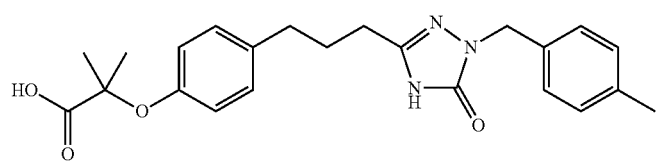
LY-674
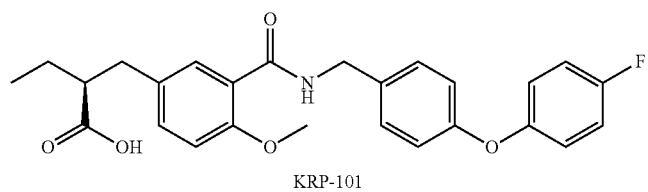
KRP-101
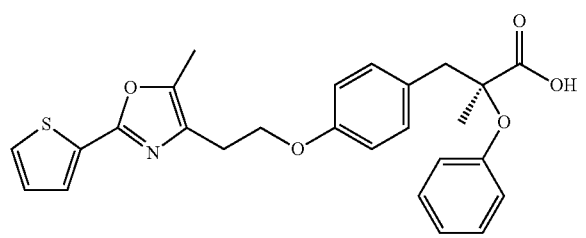
LY-510929
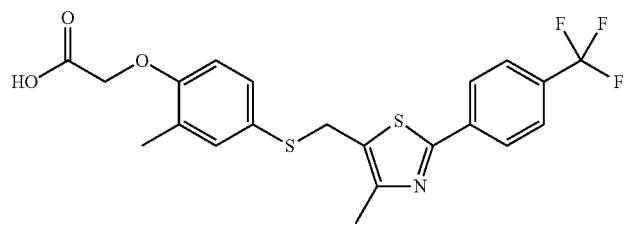
GW-501516

-continued
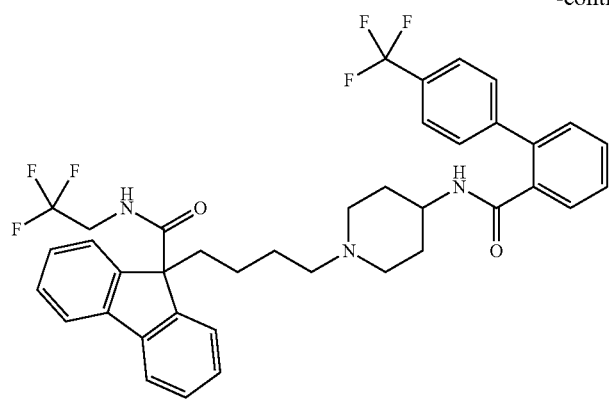
BMS-201038
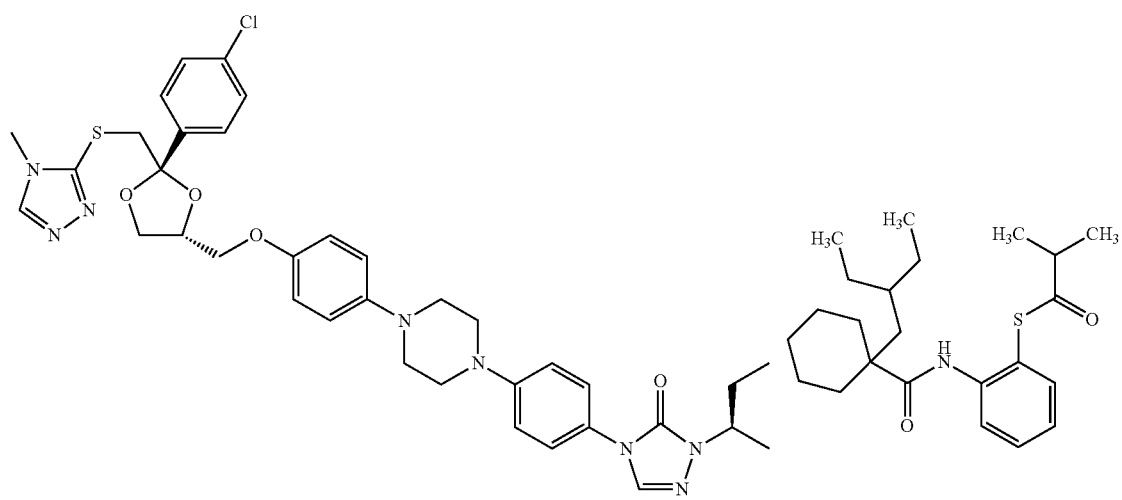
R-103757
JTT-705
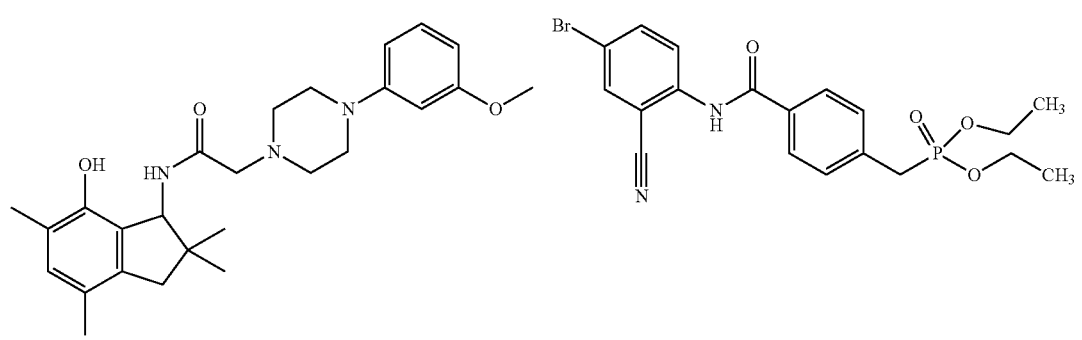
OPC-14117
NO-1886
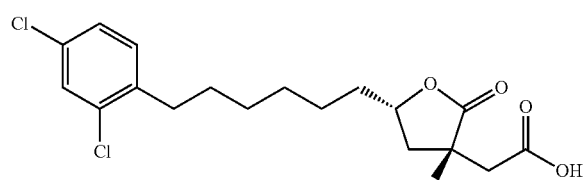
SB-204990

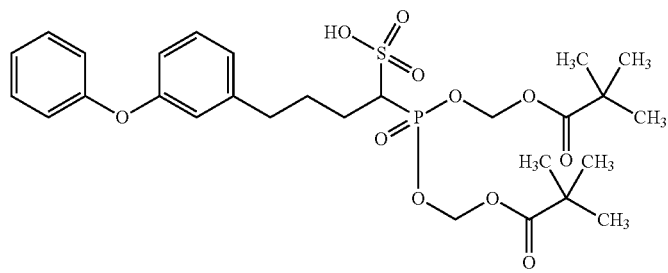
BMS-188494
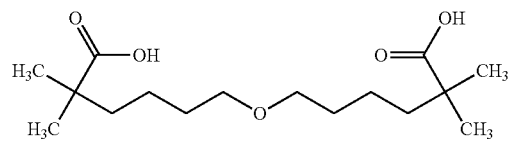
CI-1027
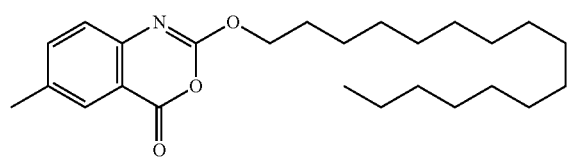
ATL-962
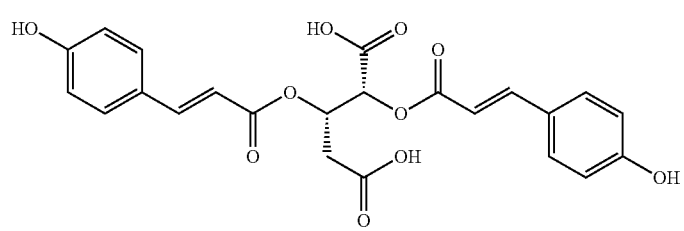
FR-258900
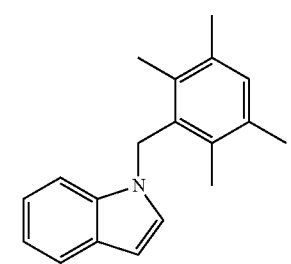
NNC-25-2504
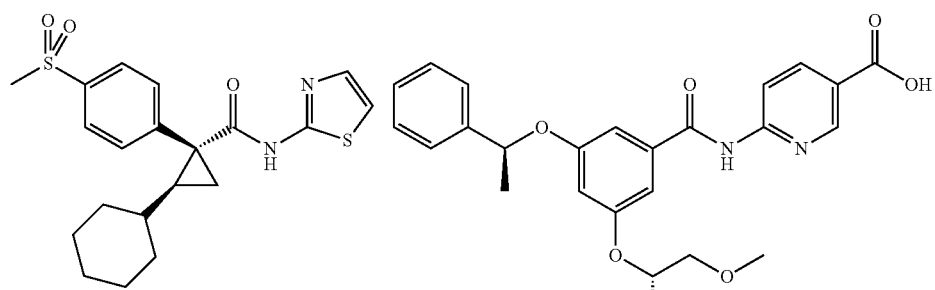
LY-2121260    GKA-50
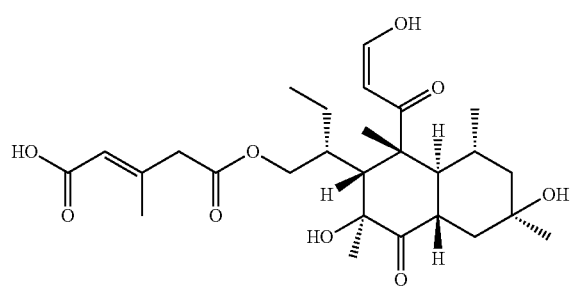
FR-225654
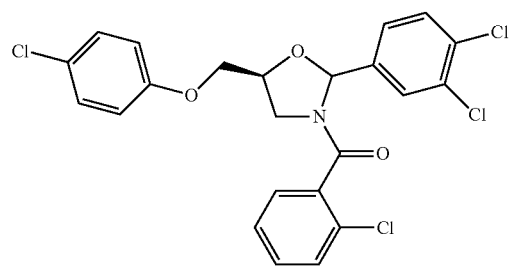
KST-48

-continued
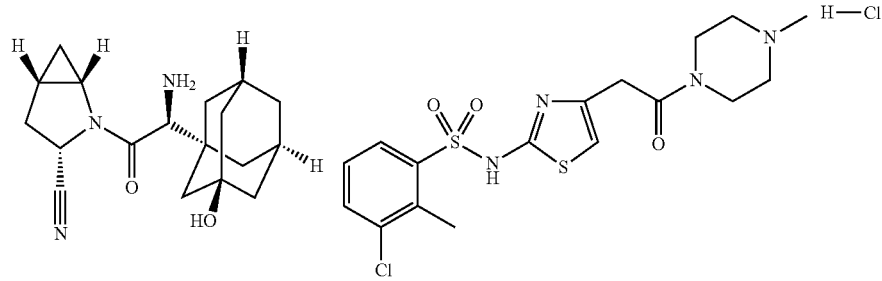
BMS-477118
BVT-2733
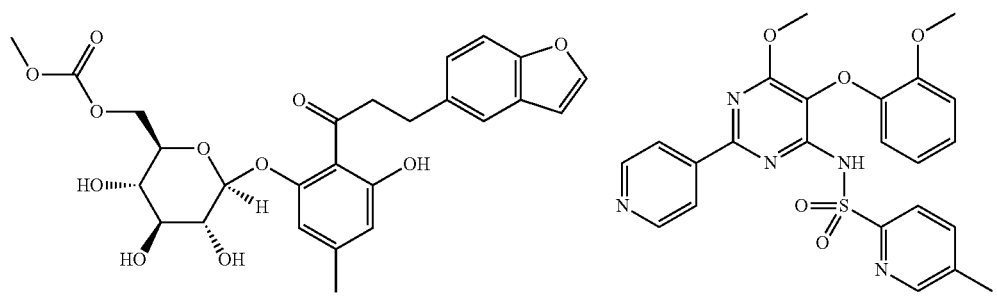
T-1095
SPP-301
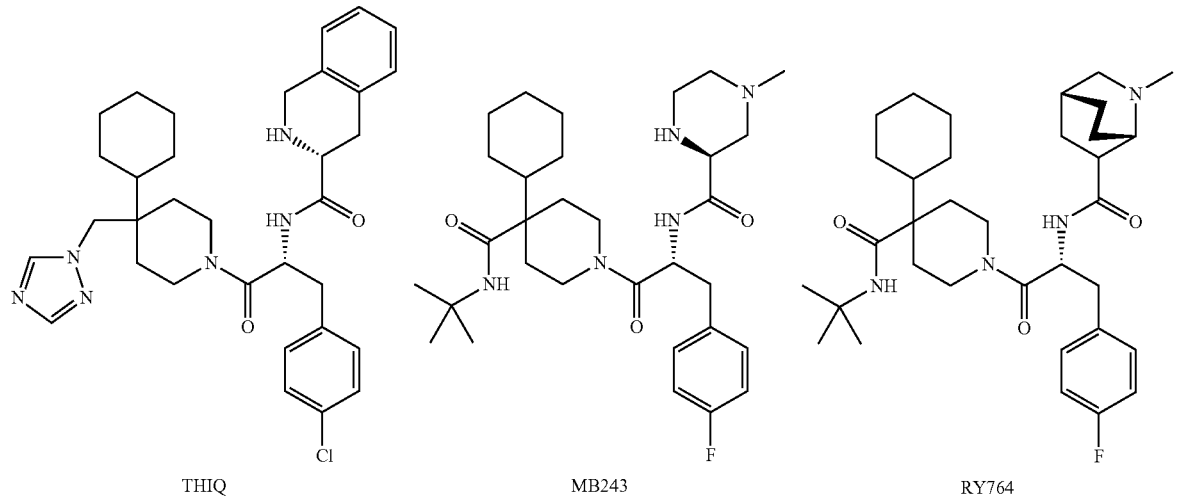
THIQ
MB243
RY764
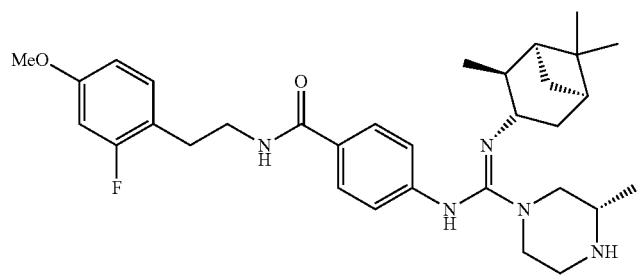
CHIR-785

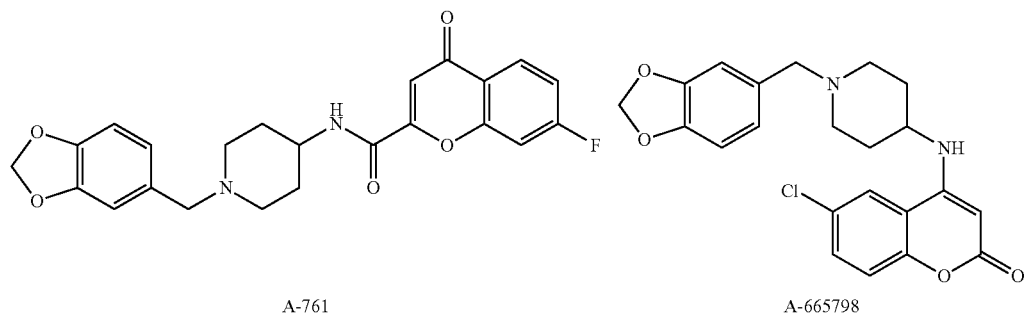
A-761
A-665798
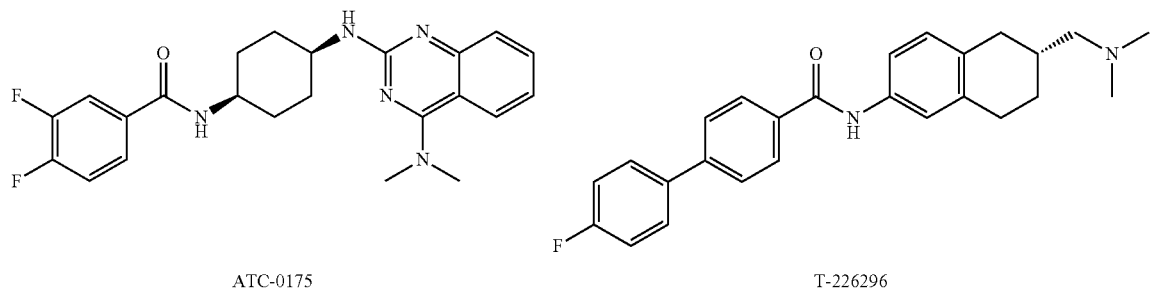
ATC-0175
T-226296
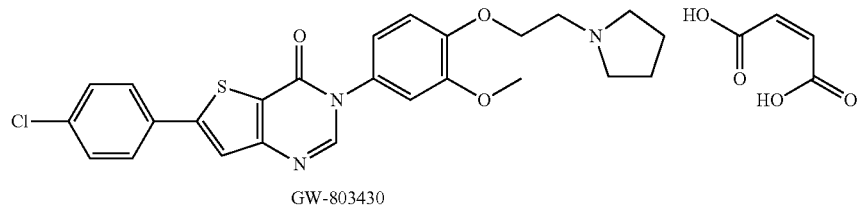
GW-803430
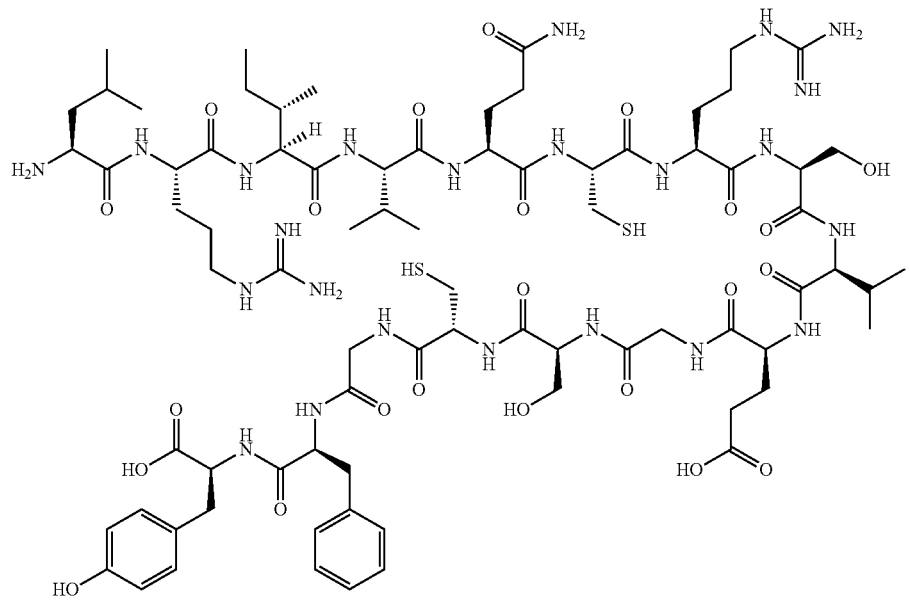
AOD-9604

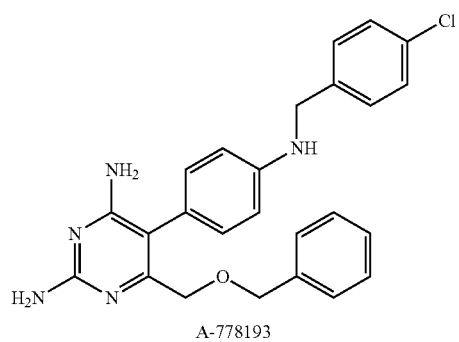
A-778193

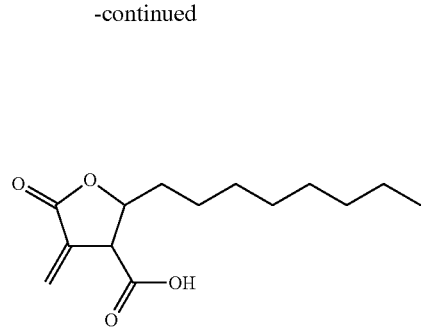
C75

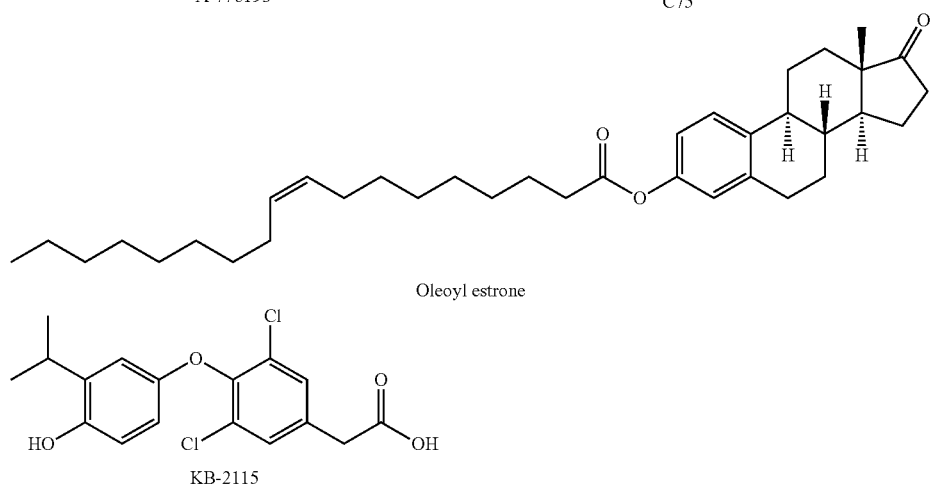
Oleoyl estrone

KB-2115

The invention further relates both to mixtures of stereoisomers of the formula I and to the pure stereoisomers of the formula I, and mixtures of diastereomers of the formula I and the pure diastereomers. Separation of the mixtures takes place chromatographically.

The examples detailed below serve to illustrate the invention without, however, restricting it.

TABLE 1

I

| Ex. | R1 | R6  | R7  | R8                 | R9  | R10 | X         | m | Linkage |
|-----|----|-----|-----|--------------------|-----|-----|-----------|---|---------|
| 1   | H  | H   | H   | F                  | H   | H   | $-(CH_2)_2-$ | 0 | 5       |
| 2   | H  | H   | CF$_3$ | H               | H   | H   | $-(CH_2)_2-$ | 0 | 5       |
| 3   | H  | H   | H   | CF$_3$             | H   | H   | $-(CH_2)_2-$ | 0 | 5       |
| 4   | H  | H   | CF$_3$ | H               | CF$_3$ | H | $-(CH_2)_2-$ | 0 | 5       |
| 5   | H  | H   | H   | NEt$_2$            | H   | H   | $-(CH_2)_2-$ | 0 | 5       |
| 6   | H  | CN  | H   | H                  | H   | H   | $-(CH_2)_2-$ | 0 | 5       |
| 7   | H  | H   | H   | SO$_2$NH$_2$       | H   | H   | $-(CH_2)_2-$ | 0 | 5       |
| 8   | H  | H   | H   | OCHF$_2$           | H   | H   | $-(CH_2)_2-$ | 0 | 5       |
| 9   | H  | Ph  | H   | H                  | H   | H   | $-(CH_2)_2-$ | 0 | 5       |
| 10  | H  | H   | H   | SO$_2$—N-Pip       | H   | H   | $-(CH_2)_2-$ | 0 | 5       |
| 11  | H  | H   | H   | SO$_2$—N-Pip       | H   | H   | $-(CH_2)_2-$ | 0 | 5       |
| 12  | H  | CF$_3$ | H | H                  | H   | H   | $-(CH_2)_2-$ | 0 | 5       |

TABLE 1-continued

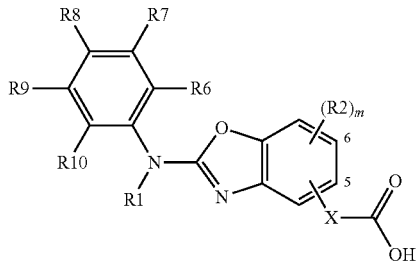

| Ex. | R1 | R6 | R7 | R8 | R9 | R10 | X | m | Linkage |
|---|---|---|---|---|---|---|---|---|---|
| 13 | H | F | H | F | H | H | —(CH$_2$)$_2$— | 0 | 5 |
| 14 | H | F | H | F | H | F | —(CH$_2$)$_2$— | 0 | 5 |
| 15 | H | F | H | H | H | F | —(CH$_2$)$_2$— | 0 | 5 |
| 16 | H | H | CF$_3$ | H | H | Cl | —(CH$_2$)$_2$— | 0 | 5 |
| 17 | H | H | CN | H | H | H | —(CH$_2$)$_2$— | 0 | 5 |
| 18 | H | H | Cl | H | H | OMe | —(CH$_2$)$_2$— | 0 | 5 |
| 19 | H | H | OMe | OMe | H | H | —(CH$_2$)$_2$— | 0 | 5 |
| 20 | H | H | OMe | OMe | OMe | H | —(CH$_2$)$_2$— | 0 | 5 |
| 21 | H | H | Ph | H | H | OMe | —(CH$_2$)$_2$— | 0 | 5 |
| 22 | H | H | H | OCH$_2$Ph | H | H | —(CH$_2$)$_2$— | 0 | 5 |
| 23 | H | H | CO$_2$H | H | H | H | —(CH$_2$)$_2$— | 0 | 5 |
| 24 | H | H | H | CO$_2$H | H | H | —(CH$_2$)$_2$— | 0 | 5 |
| 25 | H | H | H | OCF$_3$ | H | H | —(CH$_2$)$_2$— | 0 | 5 |
| 26 | H | H | OCH$_2$Ph | H | H | H | —(CH$_2$)$_2$— | 0 | 5 |
| 27 | H | H | H | OPh | H | H | —(CH$_2$)$_2$— | 0 | 5 |
| 28 | H | OCF$_3$ | H | H | H | H | —(CH$_2$)$_2$— | 0 | 5 |
| 29 | H | CF$_3$ | H | Cl | H | H | —(CH$_2$)$_2$— | 0 | 5 |
| 30 | H | H | H | SCF$_3$ | H | H | —(CH$_2$)$_2$— | 0 | 5 |
| 31 | H | H | SCF$_3$ | H | H | H | —(CH$_2$)$_2$— | 0 | 5 |
| 32 | H | H | CF$_3$ | H | H | F | —(CH$_2$)$_2$— | 0 | 5 |
| 33 | H | OCHF$_2$ | H | H | H | H | —(CH$_2$)$_2$— | 0 | 5 |
| 34 | H | Me | H | H | H | Me | —(CH$_2$)$_2$— | 0 | 5 |
| 35 | H | Br | H | Me | H | H | —(CH$_2$)$_2$— | 0 | 5 |
| 36 | H | H | Br | H | H | Br | —(CH$_2$)$_2$— | 0 | 5 |
| 37 | H | F | F | F | F | F | —(CH$_2$)$_2$— | 0 | 5 |
| 38 | H | H | H | Br | H | H | —(CH$_2$)$_2$— | 0 | 5 |
| 39 | H | H | H | N(Et)—(CH$_2$)$_2$—OH | H | H | —(CH$_2$)$_2$— | 0 | 5 |
| 40 | H | H | H | (CH$_2$)$_2$—OH | H | H | —(CH$_2$)$_2$— | 0 | 5 |
| 41 | H | H | H | NMe$_2$ | H | H | —(CH$_2$)$_2$— | 0 | 5 |
| 42 | H | H | H | SO$_3$H | H | H | —(CH$_2$)$_2$— | 0 | 5 |
| 43 | H | F | F | H | F | F | —(CH$_2$)$_2$— | 0 | 5 |
| 44 | H | H | F | H | H | F | —(CH$_2$)$_2$— | 0 | 5 |
| 45 | H | Cl | Cl | H | H | H | —(CH$_2$)$_2$— | 0 | 5 |
| 46 | H | Cl | Cl | Cl | H | H | —(CH$_2$)$_2$— | 0 | 5 |
| 47 | H | H | Cl | Cl | H | Cl | —(CH$_2$)$_2$— | 0 | 5 |
| 48 | H | Cl | H | Cl | H | Cl | —(CH$_2$)$_2$— | 0 | 5 |
| 49 | H | H | Cl | H | H | Cl | —(CH$_2$)$_2$— | 0 | 5 |
| 50 | H | H | OMe | H | H | OMe | —(CH$_2$)$_2$— | 0 | 5 |
| 51 | H | SMe | H | H | H | H | —(CH$_2$)$_2$— | 0 | 5 |
| 52 | H | Me | Me | H | H | H | —(CH$_2$)$_2$— | 0 | 5 |
| 53 | H | H | Me | Me | H | Me | —(CH$_2$)$_2$— | 0 | 5 |
| 54 | H | Et | H | H | H | H | —(CH$_2$)$_2$— | 0 | 5 |
| 55 | H | Me | H | H | H | Et | —(CH$_2$)$_2$— | 0 | 5 |
| 56 | H | Et | H | H | H | Et | —(CH$_2$)$_2$— | 0 | 5 |
| 57 | H | H | Cl | H | Cl | H | —(CH$_2$)$_2$— | 0 | 5 |
| 58 | H | H | CO$_2$Me | H | H | H | —(CH$_2$)$_2$— | 0 | 5 |
| 59 | H | H | Me | H | Me | H | —(CH$_2$)$_2$— | 0 | 5 |
| 60 | H | OMe | H | H | Me | H | —(CH$_2$)$_2$— | 0 | 5 |
| 61 | H | —CH=CH—CH=CH— | | H | H | H | —(CH$_2$)$_2$— | 0 | 5 |
| 62 | H | —CH=CH—CH=CH— | | NMe$_2$ | H | H | —(CH$_2$)$_2$— | 0 | 5 |
| 63 | H | H | H | H | H | H | —(CH$_2$)$_2$— | 0 | 5 |
| 64 | H | F | H | H | H | H | —(CH$_2$)$_2$— | 0 | 5 |
| 65 | H | Cl | H | H | H | H | —(CH$_2$)$_2$— | 0 | 5 |
| 66 | H | Me | H | H | H | H | —(CH$_2$)$_2$— | 0 | 5 |
| 67 | H | H | F | H | H | H | —(CH$_2$)$_2$— | 0 | 5 |
| 68 | H | H | Cl | H | H | H | —(CH$_2$)$_2$— | 0 | 5 |
| 69 | H | H | Me | H | H | H | —(CH$_2$)$_2$— | 0 | 5 |
| 70 | H | H | H | Cl | H | H | —(CH$_2$)$_2$— | 0 | 5 |
| 71 | H | H | H | Me | H | H | —(CH$_2$)$_2$— | 0 | 5 |
| 72 | H | OMe | H | H | H | H | —(CH$_2$)$_2$— | 0 | 5 |
| 73 | H | H | H | OMe | H | H | —(CH$_2$)$_2$— | 0 | 5 |
| 74 | H | i-Pr | H | H | H | H | —(CH$_2$)$_2$— | 0 | 5 |
| 75 | H | Me | H | Me | H | Me | —(CH$_2$)$_2$— | 0 | 5 |

TABLE 1-continued

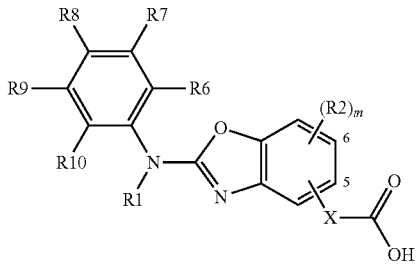

| Ex. | R1 | R6 | R7 | R8 | R9 | R10 | X | m | Linkage |
|---|---|---|---|---|---|---|---|---|---|
| 76 | H | Me | Cl | H | H | H | —(CH$_2$)$_2$— | 0 | 5 |
| 77 | H | H | Cl | Me | H | H | —(CH$_2$)$_2$— | 0 | 5 |
| 78 | H | H | H | CO$_2$Et | H | H | —(CH$_2$)$_2$— | 0 | 5 |
| 79 | H | H | H | t-Bu | H | H | —(CH$_2$)$_2$— | 0 | 5 |
| 80 | H | H | H | i-Pr | H | H | —(CH$_2$)$_2$— | 0 | 5 |
| 81 | H | H | Me | Me | H | H | —(CH$_2$)$_2$— | 0 | 5 |
| 82 | H | Cl | H | Cl | H | H | —(CH$_2$)$_2$— | 0 | 5 |
| 83 | H | H | Cl | Cl | H | H | —(CH$_2$)$_2$— | 0 | 5 |
| 84 | H | Br | H | H | H | H | —(CH$_2$)$_2$— | 0 | 5 |
| 85 | H | H | Br | H | H | H | —(CH$_2$)$_2$— | 0 | 5 |
| 86 | H | H | Cl | Br | H | H | —(CH$_2$)$_2$— | 0 | 5 |
| 87 | H | H | Ac | H | H | H | —(CH$_2$)$_2$— | 0 | 5 |
| 88 | H | Me | H | Br | H | Me | —(CH$_2$)$_2$— | 0 | 5 |
| 89 | H | H | F | Me | H | H | —(CH$_2$)$_2$— | 0 | 5 |
| 90 | H | H | F | F | H | H | —(CH$_2$)$_2$— | 0 | 5 |
| 91 | H | Cl | H | CF$_3$ | H | H | —(CH$_2$)$_2$— | 0 | 5 |
| 92 | H | H | CH$_2$OH | H | H | H | —(CH$_2$)$_2$— | 0 | 5 |
| 93 | H | H | CH(OH)—CH$_3$ | H | H | H | —(CH$_2$)$_2$— | 0 | 5 |
| 94 | H | Cl | H | F | H | H | —(CH$_2$)$_2$— | 0 | 5 |
| 95 | H | F | H | Cl | H | H | —(CH$_2$)$_2$— | 0 | 5 |
| 96 | H | H | Me | Cl | H | H | —(CH$_2$)$_2$— | 0 | 5 |
| 97 | H | Br | H | Br | H | H | —(CH$_2$)$_2$— | 0 | 5 |
| 98 | H | H | F | F | H | F | —(CH$_2$)$_2$— | 0 | 5 |
| 99 | H | F | F | H | F | H | —(CH$_2$)$_2$— | 0 | 5 |
| 100 | H | Me | F | H | H | H | —(CH$_2$)$_2$— | 0 | 5 |
| 101 | H | Br | H | CF$_3$ | H | H | —(CH$_2$)$_2$— | 0 | 5 |
| 102 | H | F | Cl | H | H | H | —(CH$_2$)$_2$— | 0 | 5 |
| 103 | H | H | Me | F | H | H | —(CH$_2$)$_2$— | 0 | 5 |
| 104 | H | H | OMe | Cl | H | OMe | —(CH$_2$)$_2$— | 0 | 5 |
| 105 | H | H | —(CH$_2$)$_3$— | | H | H | —(CH$_2$)$_2$— | 0 | 5 |
| 106 | H | Me | H | OMe | H | H | —(CH$_2$)$_2$— | 0 | 5 |
| 107 | H | H | Cl | OMe | H | OMe | —(CH$_2$)$_2$— | 0 | 5 |
| 108 | H | H | Cl | F | H | H | —(CH$_2$)$_2$— | 0 | 5 |
| 109 | H | H | —O—CH$_2$—O— | | H | H | —(CH$_2$)$_2$— | 0 | 5 |
| 110 | H | H | Et | H | H | H | —(CH$_2$)$_2$— | 0 | 5 |
| 111 | H | H | H | CN | H | H | —(CH$_2$)$_2$— | 0 | 5 |
| 112 | H | Me | H | Cl | H | H | —(CH$_2$)$_2$— | 0 | 5 |
| 113 | H | H | CF$_3$ | Cl | H | H | —(CH$_2$)$_2$— | 0 | 5 |
| 114 | H | H | H | OEt | H | H | —(CH$_2$)$_2$— | 0 | 5 |
| 115 | H | H | H | CO$_2$Me | H | H | —(CH$_2$)$_2$— | 0 | 5 |
| 116 | H | H | H | Ac | H | H | —(CH$_2$)$_2$— | 0 | 5 |
| 117 | H | H | H | Et | H | H | —(CH$_2$)$_2$— | 0 | 5 |
| 118 | H | H | H | n-Bu | H | H | —(CH$_2$)$_2$— | 0 | 5 |
| 119 | H | H | H | SMe | H | H | —(CH$_2$)$_2$— | 0 | 5 |
| 120 | H | OEt | H | H | H | H | —(CH$_2$)$_2$— | 0 | 5 |
| 121 | H | Me | H | H | Me | H | —(CH$_2$)$_2$— | 0 | 5 |
| 122 | H | H | Cl | H | H | Me | —(CH$_2$)$_2$— | 0 | 5 |
| 123 | H | Me | H | F | H | H | —(CH$_2$)$_2$— | 0 | 5 |
| 124 | H | H | —O—(CH$_2$)$_2$—O | | H | H | —(CH$_2$)$_2$— | 0 | 5 |
| 125 | H | H | F | H | H | Br | —(CH$_2$)$_2$— | 0 | 5 |
| 126 | H | Br | H | F | H | H | —(CH$_2$)$_2$— | 0 | 5 |
| 127 | H | H | OH | H | H | H | —(CH$_2$)$_2$— | 0 | 5 |
| 128 | H | Cl | H | Cl | H | Me | —(CH$_2$)$_2$— | 0 | 5 |
| 129 | H | Br | H | i-Pr | H | H | —(CH$_2$)$_2$— | 0 | 5 |
| 130 | H | H | Cl | H | H | F | —(CH$_2$)$_2$— | 0 | 5 |
| 131 | H | H | F | H | F | H | —(CH$_2$)$_2$— | 0 | 5 |
| 132 | H | F | F | F | H | H | —(CH$_2$)$_2$— | 0 | 5 |
| 133 | H | H | Cl | OH | Cl | H | —(CH$_2$)$_2$— | 0 | 5 |
| 134 | H | F | H | Br | H | H | —(CH$_2$)$_2$— | 0 | 5 |
| 135 | H | H | CF$_3$ | F | H | H | —(CH$_2$)$_2$— | 0 | 5 |
| 136 | H | H | CF$_3$ | Me | H | H | —(CH$_2$)$_2$— | 0 | 5 |
| 137 | H | H | Me | OH | Me | H | —(CH$_2$)$_2$— | 0 | 5 |
| 138 | H | Cl | Cl | H | Cl | Cl | —(CH$_2$)$_2$— | 0 | 5 |

TABLE 1-continued

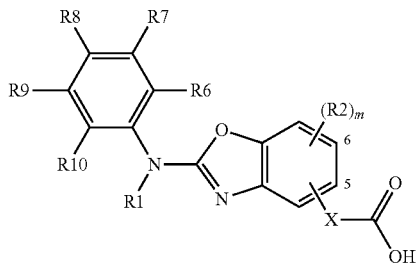

| Ex. | R1 | R6 | R7 | R8 | R9 | R10 | X | m | Linkage |
|---|---|---|---|---|---|---|---|---|---|
| 139 | H | OCHF$_2$ | H | Me | H | H | —(CH$_2$)$_2$— | 0 | 5 |
| 140 | H | OCHF$_2$ | H | H | Me | H | —(CH$_2$)$_2$— | 0 | 5 |
| 141 | H | F | H | Me | H | H | —(CH$_2$)$_2$— | 0 | 5 |
| 142 | H | F | H | H | Me | H | —(CH$_2$)$_2$— | 0 | 5 |
| 143 | H | CO$_2$H | H | H | H | H | —(CH$_2$)$_2$— | 0 | 5 |
| 144 | H | Cl | Cl | H | H | H | —(CH$_2$)$_2$— | 0 | 6 |
| 145 | H | CF$_3$ | H | Cl | H | H | —(CH$_2$)$_2$— | 0 | 6 |
| 146 | H | Cl | H | CF$_3$ | H | H | —(CH$_2$)$_2$— | 0 | 5 |

The activity of the compounds was tested as follows:
In vitro FLIPR Assay with Recombinant Cells which Express the GPCR GPR40

Function-testing assays were carried out by means of the FLIPR technique ("Fluorescence Imaging Plate Reader", Molecular Devices Corp.). For this purpose, agonist-induced changes in the intracellular concentration of Ca$^{2+}$ in recombinant HEK293 cells which expressed the GPCR GPR40 were determined.

For the investigations, cells were seeded in 96-well microliter plates (60 000 cells/well) and allowed to grow overnight. The medium was removed and the cells were incubated in buffer which contained the fluorescent dye fluo-4. After this loading with dye, the cells were washed, test substance was added, and changes in the intracellular Ca$^{2+}$ concentration were measured in the FLIPR instrument. Results have been presented as percentage change relative to the control (0%: no test substance added; 100%: 10 µM reference agonist linoleic acid added).

TABLE 2

Biological activity

| Ex. | % activation @ 100 µM |
|---|---|
| 29 | 92 |
| 36 | 97 |
| 45 | 111 |
| 48 | 111 |
| 82 | 90 |
| 91 | 100 |
| 97 | 96 |
| 101 | 96 |
| 129 | 89 |
| 138 | 100 |
| 144 | 87 |
| 145 | 79 |

It is evident from the table that the compounds of the formula I activate the GPR40 receptor and thus are very suitable for the treatment of hyperglycemia and of diabetes. Insulin release is increased by the compounds of the formula I (see Itoh et al., Nature 2003, 422, 173-176).

The compounds of the formula I may also show a corresponding effect on the GPR120 receptor.

The compounds of the formula I can be prepared for example by reacting suitable starting materials of the formula II (the syntheses are sufficiently well known in the literature) with isothiocyanates of the formula III to give compounds of the formula IV.

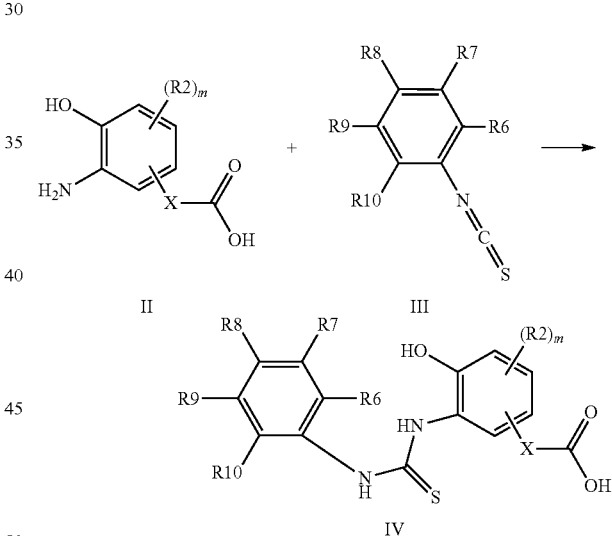

This process is adequately described in the literature.

The compounds of the formula I can be prepared for example by converting suitable starting materials (in the case of substituted (2-hydroxyphenyl)thioureas) of the formula IV (the syntheses are sufficiently well known in the literature) by a choice of a suitable desulfurizing reagent such as, for example, yellow HgO (Journal of Chemical Research, Synopses 2001, (4), 138-139), PbO (Journal of Pharmaceutical Sciences 1964, 53 (5), 538-44), AgNO$_3$/NH$_4$OH (Khimiya Geterotsiklicheskikh Soedinenii 1981, (5), 604-7), KO$_2$ (Chemistry Letters 1986, (8), 1291-4), N,N'-dicyclohexylcarbonyldiimide (DE 3006671), methyl iodide/s-collidine (Tetrahedron Letters 2001, 42 (34), 5853-5856), or p-toluenesulfonyl chloride/NaOH (Tetrahedron 2004, 60, 9883-9888) into the corresponding 2-aminobenzoxazoles of the formula I.

The compounds of the formula I can also be converted by the synthesis described by Jong Yeon Hwang and Young-Dae Gong (J. Comb. Chem. 2006, in press) of polymer-bound mercaptobenzoxazoles by reacting 2-aminophenols of the formula II with CS₂ and for example Merrifield resin in the presence of diisopropylcarbonyldiimide into the compounds of the formula V,

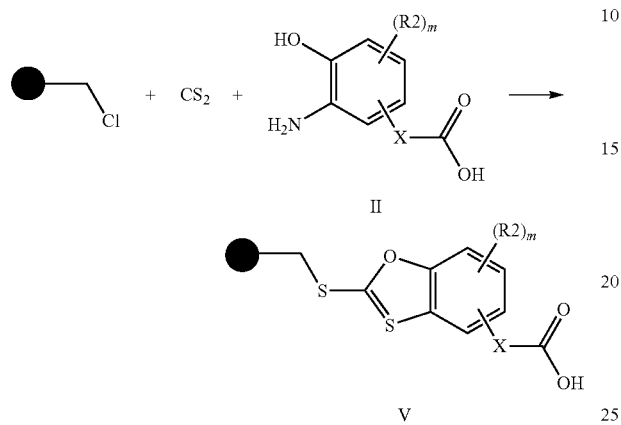

subsequent oxidation of the sulfur to the sulfone and reaction with anilines of the formula VI afford compounds of the formula I.

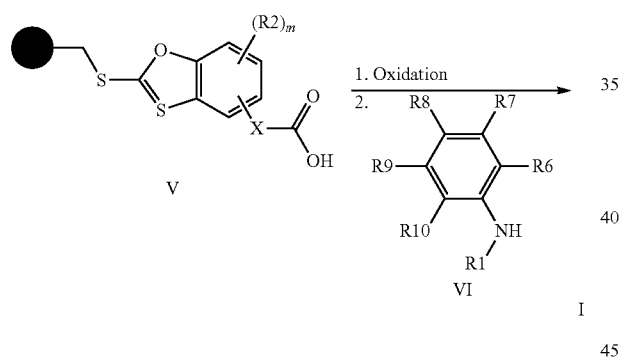

The general preparation of the examples is described in detail below:

Experimental Section:
General Experimental Protocol:

0.25 mmol of an aminophenol is dissolved in 1.5 ml of 4:1 toluene/dimethylformamide, and 0.275 mmol of the appropriate isocyanate is added. The mixture is then heated at 80° C. with stirring for 1 hour. After complete conversion into the thiourea, 0.375 mmol of yellow HgO is added and stirring is continued at 80° C. for 2 hours. After conversion is complete, the mixture is cooled and mixed with 0.3 g of thiol scavenger (SiO₂-bound propane thiol, Aldrich) and stirred at room temperature for a further 12 hours. It is then filtered through Celite, concentrated and purified by preparative HPLC (Waters C₁₈, X-Terra, 10 μm, 30×100 mm, acetonitrile/(water+ 0.1% TFA), 10% acetonitrile to 90% in 4 minutes).

The compounds were analyzed by LC/MS. The appropriate molecular peak (M+H) was detectable by LC/MS with all the examples.

We claim:

1. A method for lowering blood glucose in a patient in need thereof, comprising administering to the patient a pharmaceutically effective amount of a compound of formula I

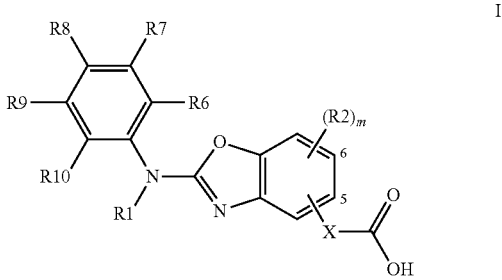

wherein:

R1 is H or $(C_1$-$C_6)$-alkyl;

R6, R7, R8, R9 and R10 are, independently of one another, H, F, Cl, Br, CN, CF₃, OH, OCF₃, OCHF₂, SCH₃, SCF₃, phenyl, O-phenyl, COOH, COO—$(C_1$-$C_6)$-alkyl, CO—$(C_1$-$C_6)$-alkyl, $(C_1$-$C_6)$-alkyl, O—$(C_1$-$C_6)$-alkyl, OBn, SO₃H, SO₂NR3R4, NR3R4 or SO₂—N-piperidinyl, wherein the alkyl and phenyl moieties are optionally substituted one or more times by R2, or two of the radicals R6, R7, R8, R9 and R10, in adjacent position on the phenyl ring may together form a radical —O—CH₂—O—, —O—(CH₂)₂—O— or —CH═CH—CH═CH—;

m is 0, 1, 2 or 3;

X is bond, $(C_2$-$C_{10})$-alkylene, $(C_3$-$C_{12})$-cycloalkyl, $(C_1$-$C_8)$-alkylene-$(C_3$-$C_{12})$-cycloalkyl-$(C_1$-$C_8)$-alkylene, $(C_1$-$C_8)$-alkylene-$(C_3$-$C_{12})$-cycloalkyl, $(C_3$-$C_{12})$-cycloalkyl-$(C_1$-$C_8)$-alkylene, $(C_2$-$C_8)$-alkenylene-$(C_3$-$C_{12})$-cycloalkyl-$(C_1$-$C_8)$-alkylene, $(C_1$-$C_8)$-alkylene-$(C_3$-$C_{12})$-cycloalkyl-$(C_2$-$C_8)$-alkenylene, $(C_2$-$C_8)$-alkenylene-$(C_3$-$C_{12})$-cycloalkyl, $(C_3$-$C_{12})$-cycloalkyl-$(C_2$-$C_8)$-alkenylene, $(C_2$-$C_{10})$-alkenylene or $(C_2$-$C_{10})$-alkynylene, wherein the alkylene, cycloalkyl, alkenylene and alkynylene moieties are optionally substituted one or more times by R5;

R2 is OH, F, Cl, Br, CN, OCH₃, OCF₃, CH₃, CF₃, $(C_1$-$C_6)$-alkyl or O—$(C_1$-$C_6)$-alkyl, wherein the alkyl moiety is optionally substituted one or more times by OH, F, Cl, Br or CN;

R3 and R4 are, independently of one another, H or $(C_1$-$C_6)$-alkyl, wherein the alkyl is optionally substituted one or more times by OH, F, Cl or Br; and R5 is NH₂, NH$(C_1$-$C_4)$-alkyl, N[$(C_1$-$C_4)$-alkyl]₂, F, Cl, Br, CN, OH, O—$(C_1$-$C_6)$-alkyl, $(C_1$-$_6)$-alkyl, $(C_2$-$C_6)$-alkenyl or $(C_2$-$C_6)$-alkynyl, or a physiologically tolerated salt thereof.

2. A method for lowering blood glucose in a patient in need thereof, comprising administering to the patient a pharmaceutically effective amount of a compound of formula I

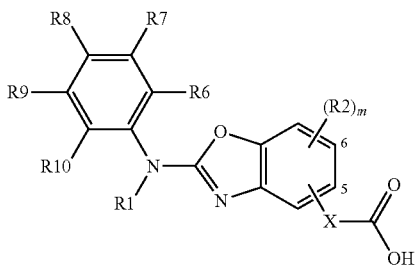

wherein:
R1 is H or ($C_1$-$C_6$)-alkyl;
R6, R7, R8, R9 and R10 are, independently of one another, H, F, Cl, Br, $CF_3$, $OCH_3$, $OCF_3$, $OCHF_2$, $SCH_3$, $SCF_3$, phenyl, ($C_1$-$C_6$)-alkyl, O—($C_1$-$C_6$)-alkyl or NR3R4, wherein the alkyl and phenyl moieties are optionally substituted one or more times by R2, or
two of the radicals R6, R7, R8, R9 and R10 in adjacent position on the phenyl ring may together form a radical —CH=CH—CH=CH—;
m is 0, 1, 2 or 3;
X is ($C_2$-$C_{10}$)-alkylene, which is optionally substituted one or more times by R5;
R2 is F, Cl, Br, CN, $OCH_3$, $OCF_3$, $CH_3$, $CF_3$, ($C_1$-$C_6$)-alkyl or O—($C_1$-$C_6$)-alkyl, wherein the alkyl moiety is optionally substituted one or more times by OH, F, Cl, Br or CN;
R3 and R4 are, independently of one another, H or ($C_1$-$C_6$)-alkyl; and
R5 is $NH_2$, NH($C_1$-$C_4$)-alkyl, N[($C_1$-$C_4$)-alkyl]$_2$, F, Cl, Br, CN, OH, O—($C_1$-$C_6$)-alkyl, ($C_{1\text{-}6}$)-alkyl, ($C_2$-$C_6$)-alkenyl or ($C_2$-$C_6$)-alkynyl,
or a physiologically tolerated salt thereof.

3. A method for lowering blood glucose in a patient in need thereof, comprising administering to the patient a pharmaceutically effective amount of a compound of formula I

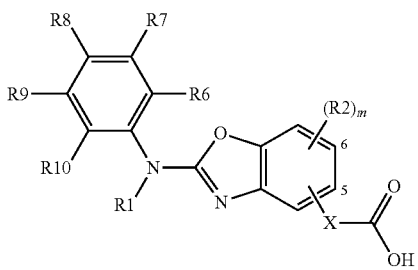

wherein:
R1 is H;
R6, R7, R8, R9 and R10 are, independently of one another, H, F, Cl, Br, $CF_3$, $OCH_3$, $OCF_3$, $OCHF_2$, $SCH_3$, $SCF_3$, phenyl, ($C_1$-$C_6$)-alkyl, O—($C_1$-$C_6$)-alkyl or NR3R4, wherein the alkyl and phenyl moieties are optionally substituted one or more times by R2, or
two of the radicals R6, R7, R8, R9 and R10 in adjacent position on the phenyl ring may together form a radical —CH=CH—CH=CH—;
m is 0, 1, 2 or 3;
X is —($CH_2$)$_2$—;
R2 is F, Cl, Br, CN, $OCH_3$, $OCF_3$, $CH_3$, $CF_3$, ($C_1$-$C_6$)-alkyl or O—($C_1$-$C_6$)-alkyl, wherein the alkyl moiety is optionally substituted one or more times by OH, F, Cl, Br or CN;
R3 and R4 are, independently of one another, H or ($C_1$-$C_6$)-alkyl; and
R5 is $NH_2$, NH($C_1$-$C_4$)-alkyl, N[($C_1$-$C_4$)-alkyl]$_2$, F, Cl, Br, CN, OH, O—($C_1$-$C_6$)-alkyl, ($C_{1\text{-}6}$)-alkyl, ($C_2$-$C_6$)-alkenyl or ($C_2$-$C_6$)-alkynyl,
or a physiologically tolerated salt thereof.

4. The method of claim 1,
wherein
R1 is H;
R6 is $CF_3$;
R7 is H;
R8 is Cl;
R9 is H;
R10 is H;
X is —($CH_2$)$_2$—, wherein X is linked to the carbon labelled as 5; and
m is 0,
or a physiologically tolerated salt thereof.

5. A method for treating type 2 diabetes in a patient in need thereof, comprising administering to the patient a pharmaceutically effective amount of a compound of formula I

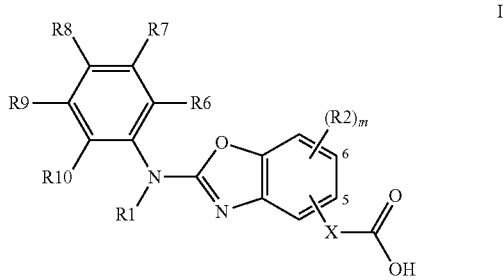

wherein:
R1 is H or ($C_1$-$C_6$)-alkyl;
R6, R7, R8, R9 and R10 are, independently of one another, H, F, Cl, Br, CN, $CF_3$, OH, $OCF_3$, $OCHF_2$, $SCH_3$, $SCF_3$, phenyl, O-phenyl, COOH, COO—($C_1$-$C_6$)-alkyl, CO—($C_1$-$C_6$)-alkyl, ($C_1$-$C_6$)-alkyl, O—($C_1$-$C_6$)-alkyl, OBn, $SO_3H$, $SO_2NR3R4$, NR3R4 or $SO_2$—N-piperidinyl, wherein the alkyl and phenyl moieties are optionally substituted one or more times by R2, or
two of the radicals R6, R7, R8, R9 and R10, in adjacent position on the phenyl ring may together form a radical —O—$CH_2$—O—, —O—($CH_2$)$_2$—O— or —CH=CH—CH=CH—;
m is 0, 1, 2 or 3;
X is bond, ($C_2$-$C_{10}$)-alkylene, ($C_3$-$C_{12}$)-cycloalkyl, ($C_1$-$C_8$)-alkylene-($C_3$-$C_{12}$)-cycloalkyl-($C_1$-$C_8$)-alkylene, ($C_1$-$C_8$)-alkylene-($C_3$-$C_{12}$)-cycloalkyl, ($C_3$-$C_{12}$)-cycloalkyl-($C_1$-$C_8$)-alkylene, ($C_2$-$C_8$)-alkenylene-($C_3$-$C_{12}$)-cycloalkyl-($C_1$-$C_8$)-alkylene, ($C_1$-$C_8$)-alkylene-($C_3$-$C_{12}$)-cycloalkyl-($C_2$-$C_8$)-alkenylene, ($C_2$-$C_8$)-alkenylene-($C_3$-$C_{12}$)-cycloalkyl, ($C_3$-$C_{12}$)-cycloalkyl-($C_2$-$C_8$)-alkenylene, ($C_2$-$C_{10}$)-alkenylene or ($C_2$-$C_{10}$)-alkynylene, wherein the alkylene, cycloalkyl, alkenylene and alkynylene moieties are optionally substituted one or more times by R5;
R2 is OH, F, Cl, Br, CN, $OCH_3$, $OCF_3$, $CH_3$, $CF_3$, ($C_1$-$C_6$)-alkyl or O—($C_1$-$C_6$)-alkyl, wherein the alkyl moiety is optionally substituted one or more times by OH, F, Cl, Br or CN;

R3 and R4 are, independently of one another, H or (C$_1$-C$_6$)-alkyl, wherein the alkyl is optionally substituted one or more times by OH, F, Cl or Br; and R5 is NH$_2$, NH(C$_1$-C$_4$)-alkyl, N[(C$_1$-C$_4$)-alkyl]$_2$, F, Cl, Br, CN, OH, O—(C$_1$-C$_6$)-alkyl, (C$_{1-6}$)-alkyl, (C$_2$-C$_6$)-alkenyl or (C$_2$-C$_6$)-alkynyl, or a physiologically tolerated salt thereof.

6. The method of claim 5,
wherein
R1 is H;
R6 is CF$_3$;
R7 is H;
R8 is Cl;
R9 is H;
R10 is H;
X is —(CH$_2$)$_2$—, wherein X is linked to the carbon labelled as 5; and
m is 0, or a physiologically tolerated salt thereof.

7. A method for treating type 2 diabetes in a patient in need thereof, comprising administering to the patient a pharmaceutically effective amount of a compound of formula I

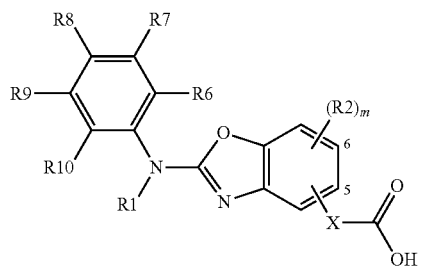

wherein:
R1 is H or (C$_1$-C$_6$)-alkyl;
R6, R7, R8, R9 and R10 are, independently of one another, H, F, Cl, Br, CF$_3$, OCH$_3$, OCF$_3$, OCHF$_2$, SCH$_3$, SCF$_3$, phenyl, (C$_1$-C$_6$)-alkyl, O—(C$_1$-C$_6$)-alkyl or NR3R4, wherein the alkyl and phenyl moieties are optionally substituted one or more times by R2, or
two of the radicals R6, R7, R8, R9 and R10 in adjacent position on the phenyl ring may together form a radical —CH=CH—CH=CH—;
m is 0, 1, 2 or 3;
X is (C$_2$-C$_{10}$)-alkylene, which is optionally substituted one or more times by R5;
R2 is F, Cl, Br, CN, OCH$_3$, OCF$_3$, CH$_3$, CF$_3$, (C$_1$-C$_6$)-alkyl or O—(C$_1$-C$_6$)-alkyl, wherein the alkyl moiety is optionally substituted one or more times by OH, F, Cl, Br or CN;
R3 and R4 are, independently of one another, H or (C$_1$-C$_6$)-alkyl; and
R5 is NH$_2$, NH(C$_1$-C$_4$)-alkyl, N[(C$_1$-C$_4$)-alkyl]$_2$, F, Cl, Br, CN, OH, O—(C$_1$-C$_6$)-alkyl, (C$_{1-6}$)-alkyl, (C$_2$-C$_6$)-alkenyl or (C$_2$-C$_6$)-alkynyl, or a physiologically tolerated salt thereof.

8. A method for treating type 2 diabetes, in a patient in need thereof, comprising administering to the patient a pharmaceutically effective amount of a compound of formula I

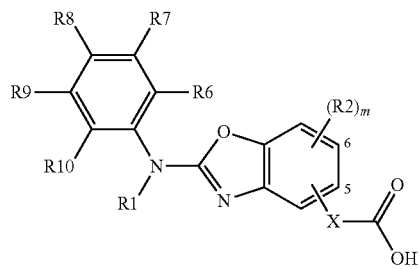

wherein:
R1 is H;
R6, R7, R8, R9 and R10 are, independently of one another, H, F, Cl, Br, CF$_3$, OCH$_3$, OCF$_3$, OCHF$_2$, SCH$_3$, SCF$_3$, phenyl, (C$_1$-C$_6$)-alkyl, O—(C$_1$-C$_6$)-alkyl or NR3R4, wherein the alkyl and phenyl moieties are optionally substituted one or more times by R2, or
two of the radicals R6, R7, R8, R9 and R10 in adjacent position on the phenyl ring may together form a radical —CH=CH—CH=CH—;
m is 0, 1, 2 or 3;
X is —(CH$_2$)$_2$—;
R2 is F, Cl, Br, CN, OCH$_3$, OCF$_3$, CH$_3$, CF$_3$, (C$_1$-C$_6$)-alkyl or O—(C$_1$-C$_6$)-alkyl, wherein the alkyl moiety is optionally substituted one or more times by OH, F, Cl, Br or CN;
R3 and R4 are, independently of one another, H or (C$_1$-C$_6$)-alkyl; and
R5 is NH$_2$, NH(C$_1$-C$_4$)-alkyl, N[(C$_1$-C$_4$)-alkyl]$_2$, F, Cl, Br, CN, OH, O—(C$_1$-C$_6$)-alkyl, (C$_{1-6}$)-alkyl, (C$_2$-C$_6$)-alkenyl or (C$_2$-C$_6$)-alkynyl, or a physiologically tolerated salt thereof.

9. A method for increasing insulin release in a patient in need thereof, comprising administering to the patient a pharmaceutically effective amount of a compound of formula I

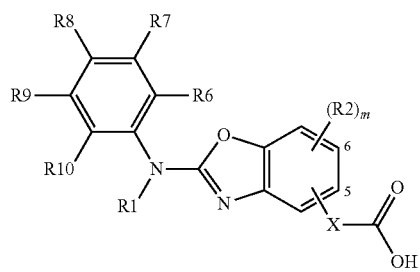

wherein:
R1 is H or (C$_1$-C$_6$)-alkyl;
R6, R7, R8, R9 and R10 are, independently of one another, H, F, Cl, Br, CN, CF$_3$, OH, OCF$_3$, OCHF$_2$, SCH$_3$, SCF$_3$, phenyl, O-phenyl, COOH, COO—(C$_1$-C$_6$)-alkyl, CO—(C$_1$-C$_6$)-alkyl, (C$_1$-C$_6$)-alkyl, O—(C$_1$-C$_6$)-alkyl, OBn, SO$_3$H, SO$_2$NR3R4, NR3R4 or SO$_2$—N-piperidinyl, wherein the alkyl and phenyl moieties are optionally substituted one or more times by R2, or
two of the radicals R6, R7, R8, R9 and R10, in adjacent position on the phenyl ring may together form a radical —O—CH$_2$—O—, —O—(CH$_2$)$_2$—O— or —CH=CH—CH=CH—;
m is 0, 1, 2 or 3;

X is bond, $(C_2-C_{10})$-alkylene, $(C_3-C_{12})$-cycloalkyl, $(C_1-C_8)$-alkylene-$(C_3-C_{12})$-cycloalkyl-$(C_1-C_8)$-alkylene, $(C_1-C_8)$-alkylene-$(C_3-C_{12})$-cycloalkyl, $(C_3-C_{12})$-cycloalkyl-$(C_1-C_8)$-alkylene, $(C_2-C_8)$-alkenylene-$(C_3-C_{12})$-cycloalkyl-$(C_1-C_8)$-alkylene, $(C_1-C_8)$-alkylene-$(C_3-C_{12})$-cycloalkyl-$(C_2-C_8)$-alkenylene, $(C_2-C_8)$-alkenylene-$(C_3-C_{12})$-cycloalkyl, $(C_3-C_{12})$-cycloalkyl-$(C_2-C_8)$-alkenylene, $(C_2-C_{10})$-alkenylene or $(C_2-C_{10})$-alkynylene, wherein the alkylene, cycloalkyl, alkenylene and alkynylene moieties are optionally substituted one or more times by R5;

R2 is OH, F, Cl, Br, CN, $OCH_3$, $OCF_3$, $CH_3$, $CF_3$, $(C_1-C_6)$-alkyl or O—$(C_1-C_6)$-alkyl, wherein the alkyl moiety is optionally substituted one or more times by OH, F, Cl, Br or CN;

R3 and R4 are, independently of one another, H or $(C_1-C_6)$-alkyl, wherein the alkyl is optionally substituted one or more times by OH, F, Cl or Br; and R5 is $NH_2$, $NH(C_1-C_4)$-alkyl, $N[(C_1-C_4)$-alkyl$]_2$, F, Cl, Br, CN, OH, O—$(C_1-C_6)$-alkyl, $(C_{1-6})$-alkyl, $(C_2-C_6)$-alkenyl or $(C_2-C_6)$-alkynyl, or a physiologically tolerated salt thereof.

10. The method of claim 9,
wherein
R1 is H;
R6 is $CF_3$;
R7 is H;
R8 is Cl;
R9 is H;
R10 is H;
X is —$(CH_2)_2$—, wherein X is linked to the carbon labelled as 5; and
m is 0,
or a physiologically tolerated salt thereof.

11. A method for increasing insulin release in a patient in need thereof, comprising administering to the patient a pharmaceutically effective amount of a compound of formula I

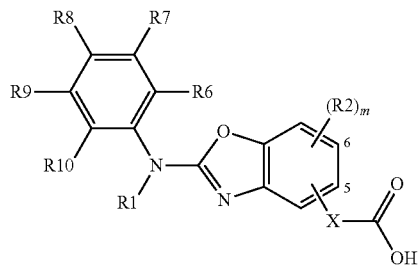

wherein:
R1 is H or $(C_1-C_6)$-alkyl;
R6, R7, R8, R9 and R10 are, independently of one another, H, F, Cl, Br, $CF_3$, $OCH_3$, $OCF_3$, $OCHF_2$, $SCH_3$, $SCF_3$, phenyl, $(C_1-C_6)$-alkyl, O—$(C_1-C_6)$-alkyl or NR3R4, wherein the alkyl and phenyl moieties are optionally substituted one or more times by R2, or two of the radicals R6, R7, R8, R9 and R10 in adjacent position on the phenyl ring may together form a radical —CH═CH—CH═CH—;

m is 0, 1, 2 or 3;
X is $(C_2-C_{10})$-alkylene, which is optionally substituted one or more times by R5;

R2 is F, Cl, Br, CN, $OCH_3$, $OCF_3$, $CH_3$, $CF_3$, $(C_1-C_6)$-alkyl or O—$(C_1-C_6)$-alkyl, wherein the alkyl moiety is optionally substituted one or more times by OH, F, Cl, Br or CN;

R3 and R4 are, independently of one another, H or $(C_1-C_6)$-alkyl; and

R5 is $NH_2$, $NH(C_1-C_4)$-alkyl, $N[(C_1-C_4)$-alkyl$]_2$, F, Cl, Br, CN, OH, O—$(C_1-C_6)$-alkyl, $(C_{1-6})$-alkyl, $(C_2-C_6)$-alkenyl or $(C_2-C_6)$-alkynyl, or a physiologically tolerated salt thereof.

12. A method for increasing insulin release in a patient in need thereof, comprising administering to the patient a pharmaceutically effective amount of a compound of formula I

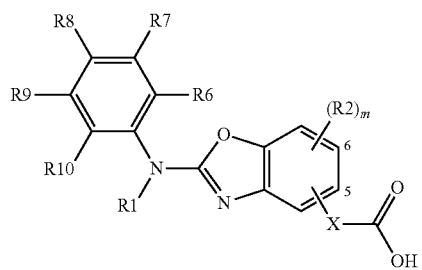

wherein:
R1 is H;
R6, R7, R8, R9 and R10 are, independently of one another, H, F, Cl, Br, $CF_3$, $OCH_3$, $OCF_3$, $OCHF_2$, $SCH_3$, $SCF_3$, phenyl, $(C_1-C_6)$-alkyl, O—$(C_1-C_6)$-alkyl or NR3R4, wherein the alkyl and phenyl moieties are optionally substituted one or more times by R2, or two of the radicals R6, R7, R8, R9 and R10 in adjacent position on the phenyl ring may together form a radical —CH═CH—CH═CH—;

m is 0, 1, 2 or 3;
X is —$(CH_2)_2$—;
R2 is F, Cl, Br, CN, $OCH_3$, $OCF_3$, $CH_3$, $CF_3$, $(C_1-C_6)$-alkyl or O—$(C_1-C_6)$-alkyl, wherein the alkyl moiety is optionally substituted one or more times by OH, F, Cl, Br or CN;

R3 and R4 are, independently of one another, H or $(C_1-C_6)$-alkyl; and

R5 is $NH_2$, $NH(C_1-C_4)$-alkyl, $N[(C_1-C_4)$-alkyl$]_2$, F, Cl, Br, CN, OH, O—$(C_1-C_6)$-alkyl, $(C_{1-6})$-alkyl, $(C_2-C_6)$-alkenyl or $(C_2-C_6)$-alkynyl, or a physiologically tolerated salt thereof.

* * * * *